United States Patent
Wang

(10) Patent No.: US 12,361,544 B2
(45) Date of Patent: Jul. 15, 2025

(54) DETECTION RESULT OUTPUT METHOD, ELECTRONIC DEVICE AND MEDIUM

(71) Applicant: VIVO MOBILE COMMUNICATION CO., LTD., Guangdong (CN)

(72) Inventor: Qiang Wang, Guangdong (CN)

(73) Assignee: VIVO MOBILE COMMUNICATION CO., LTD., Guangdong (CN)

(*) Notice: Subject to any disclaimer, the term of this patent is extended or adjusted under 35 U.S.C. 154(b) by 368 days.

(21) Appl. No.: 17/948,530

(22) Filed: Sep. 20, 2022

(65) Prior Publication Data

US 2023/0014409 A1    Jan. 19, 2023

Related U.S. Application Data

(63) Continuation of application No. PCT/CN2021/081452, filed on Mar. 18, 2021.

(30) Foreign Application Priority Data

Mar. 25, 2020 (CN) .......................... 202010218894.7

(51) Int. Cl.
*G06V 10/60* (2022.01)
*A61B 5/00* (2006.01)
(Continued)

(52) U.S. Cl.
CPC .......... *G06T 7/0012* (2013.01); *A61B 5/0033* (2013.01); *A61B 5/0064* (2013.01);
(Continued)

(58) Field of Classification Search
CPC ......... G06T 7/0012; G06T 2207/30088; G06T 2207/30201; G06T 2207/30168;
(Continued)

(56) References Cited

U.S. PATENT DOCUMENTS

2007/0064979 A1* 3/2007 Chhibber ............. G06V 10/143
382/118
2009/0161962 A1* 6/2009 Gallagher ............... G06F 16/58
382/203

(Continued)

FOREIGN PATENT DOCUMENTS

CN    2016181181 A    10/2016
CN    108063884 A      5/2018
(Continued)

OTHER PUBLICATIONS

Makarand Tapaswi, Omkar M. Parkhi, Esa Rahtu, Eric Sommerlade, Rainer Stiefelhagen, Andrew Zisserman, Total Cluster: A person agnostic clustering method for broadcast videos, Dec. 14-18, 2014, Bangalore, India.

(Continued)

*Primary Examiner* — Huo Long Chen
(74) *Attorney, Agent, or Firm* — Price Heneveld LLP

(57) ABSTRACT

A detection result output method, an electronic device, and a medium are provided. The detection result output method includes: obtaining first image information of a first object, where the first image information includes skin information of the first object; outputting a target detection result in a case that a matching degree between a first image and a target image meets a first preset condition; and outputting a first detection result in a case that the matching degree between the first image and the target image does not meet the first preset condition. The target detection result is a detection result corresponding to the target image, and the first detection result is a detection result corresponding to the first image.

15 Claims, 3 Drawing Sheets

(51) Int. Cl.
*G06T 7/00* (2017.01)
*G06V 10/75* (2022.01)

(52) U.S. Cl.
CPC .............. *A61B 5/442* (2013.01); *G06V 10/60* (2022.01); *G06V 10/751* (2022.01); *G06T 2207/30088* (2013.01); *G06T 2207/30201* (2013.01)

(58) Field of Classification Search
CPC ... G06T 7/0014; A61B 5/0033; A61B 5/0064; A61B 5/442; A61B 5/0077; A61B 5/1112; A61B 5/1176; A61B 5/7221; A61B 5/7246; A61B 5/441; G06V 10/60; G06V 10/751; G06V 40/10; G06V 40/172; G06V 10/761; G16H 30/20; G16H 40/63; G16H 50/70; G16H 30/40; G16H 50/20; G06F 18/22

See application file for complete search history.

(56) References Cited

U.S. PATENT DOCUMENTS

| | | |
|---|---|---|
| 2010/0254575 A1 | 10/2010 | Machida |
| 2018/0137344 A1 | 5/2018 | Kusakabe |
| 2019/0122024 A1 | 4/2019 | Schwartz et al. |
| 2019/0294900 A1 | 9/2019 | Li et al. |
| 2019/0340421 A1 | 11/2019 | Boenapalli et al. |

FOREIGN PATENT DOCUMENTS

| | | |
|---|---|---|
| CN | 109330560 A | 2/2019 |
| CN | 109414177 A | 3/2019 |
| CN | 109558773 A | 4/2019 |
| CN | 109840476 A | 6/2019 |
| CN | 110298304 A | 10/2019 |
| CN | 110380864 A | 10/2019 |
| CN | 111401463 A | 7/2020 |
| EP | 3412200 A1 | 12/2018 |
| JP | 2010245707 A | 10/2010 |
| JP | 201881402 A | 5/2018 |
| KR | 20150071424 A | 6/2015 |

OTHER PUBLICATIONS

Y. Yusoff, W. Christmas, and J. Kittler, A Study on Automatic Shot Change Detection, Centre for Vision, Speech and Signal Processing, University of Surrey, Guildford GU2 5XH, UK.

* cited by examiner

DETECTION RESULT OUTPUT METHOD, ELECTRONIC DEVICE AND MEDIUM

CROSS-REFERENCE TO RELATED APPLICATIONS

This application is a continuation application of International Application No. PCT/CN2021/081452 filed on Mar. 18, 2021, which claims priority to Chinese Patent Application No. 202010218894.7 filed in China on Mar. 25, 2020, which are incorporated herein by reference in their entireties.

TECHNICAL FIELD

Embodiments of the present invention relate to the field of Internet technologies, and in particular, to a detection result output method, an electronic device, and a medium.

BACKGROUND

With the continuous development of Internet technologies, an electronic device may obtain a user's skin data by collecting the user's facial image information, then detect the user's skin data, generate a skin detection result, and display the result to the user.

However, due to different shooting angles of the user, the electronic device may obtain a plurality of collected images from the different angles. However, in the prior art, when the electronic device detects skin information in the collected images, skin detection is performed on each of the collected images from different angles to obtain the skin detection result. Although the shooting angles are different, the skin detection results of a same user are generally the same.

Therefore, a manner for performing skin detection on each of the collected images in the prior art greatly reduces an output speed of the detection result of the electronic device, and has poor user experience.

SUMMARY

Embodiments of the present invention provide a detection result output method, an electronic device, and a medium, which can improve an output speed of the detection result of the electronic device and improve user experience.

According to a first aspect, an embodiment of the present invention provides a detection result output method, applied to an electronic device, including:
  obtaining first image information of a first object, where the first image information includes skin information of the first object;
  outputting a target detection result in a case that a matching degree between a first image and a target image meets a first preset condition; and
  outputting a first detection result in a case that the matching degree between the first image and the target image does not meet the first preset condition, where the target detection result is a detection result corresponding to the target image, and the first detection result is a detection result corresponding to the first image.

According to a second aspect, an embodiment of the present invention provides an electronic device, including:
  an obtaining module, configured to obtain first image information of a first object, where the first image information includes skin information of the first object;
  a first outputting module, configured to output a target detection result in a case that a matching degree between a first image and a target image meets a first preset condition; and
  a second outputting module, configured to output a first detection result in a case that the matching degree between the first image and the target image does not meet the first preset condition, where the target detection result is a detection result corresponding to the target image, and the first detection result is a detection result corresponding to the first image.

According to a third aspect, an embodiment of the present invention provides an electronic device, including a processor, a memory, and a computer program stored in the memory and capable of running on the processor. When the computer program is executed by the processor, the steps of the detection result output method according to the first aspect are implemented.

According to a fourth aspect, an embodiment of the present invention provides a computer-readable storage medium, where the computer-readable storage medium stores a computer program, and when the computer program is executed by a processor, the steps of the detection result output method according to the first aspect are implemented.

In the embodiments of the present invention, the electronic device obtains the first image information (including the skin information) of the first object, and determines the matching degree between the first image and the target image. In the case that the matching degree between the first image and the target image does not meet the first preset condition, the first detection result corresponding to the first image is output; or in the case that the matching degree between the first image and the target image meets the first preset condition, the skin detection may not be performed on the first object, and the detection result corresponding to the target object is directly output, thereby improving the output speed of the detection result of the electronic device and improving user experience.

BRIEF DESCRIPTION OF DRAWINGS

It may be better understood from the following descriptions of specific implementations of the present invention with reference to the accompanying drawings that same or similar reference numerals represent same or similar features in the present invention.

DETAILED DESCRIPTION OF EMBODIMENTS

The following clearly and completely describes the technical solutions in the embodiments of the present invention with reference to the accompanying drawings in the embodiments of the present invention. Apparently, the described embodiments are some rather than all of the embodiments of the present invention. All other embodiments obtained by a person of ordinary skill in the art based on the embodiments of the present invention without creative efforts shall fall within the protection scope of the present invention.

To resolve the problems existing in the prior art, the embodiments of the present invention provide a detection result output method, an electronic device, and a medium, which can improve an output speed of the detection result of the electronic device and improve user experience.

Figure 1:
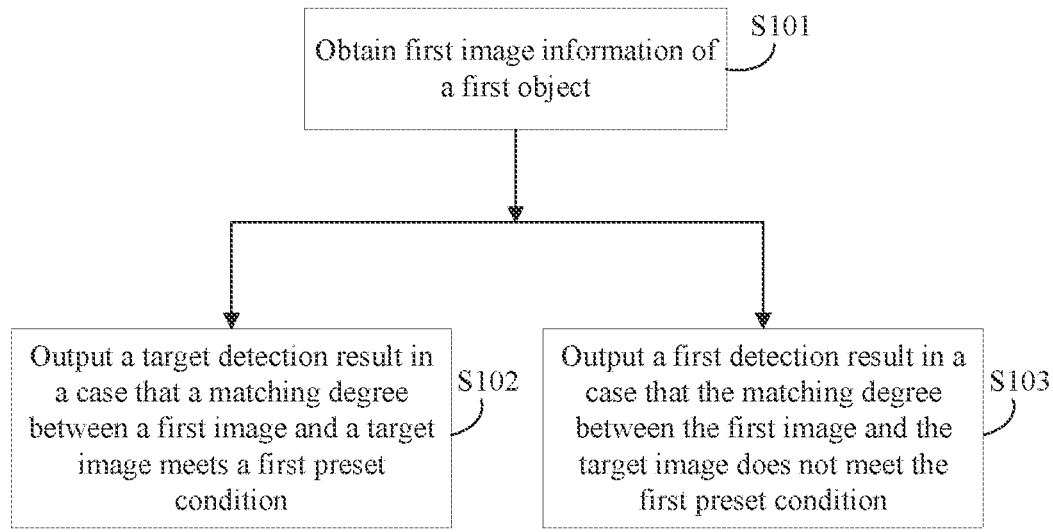
FIG. 1 is a schematic flowchart of a detection result output method according to an embodiment of the present invention.

FIG. 1 is a schematic flowchart of a detection result output method according to an embodiment of the present invention. As shown in FIG. 1, the detection result output method applied to an electronic device includes: S101, S102 and S103.

S101: Obtain first image information of a first object.

The first image information includes skin information of the first object, and the first image information further includes a first image.

Optionally, in some embodiments of the present invention, the first object may be a human, and the skin information may include, but is not limited to, the following: skin moisture, elasticity index, oiliness index, or the like.

The electronic device may obtain the first image corresponding to the first object by using a camera component, and may also store the first image in an image database corresponding to the first object.

S102: Output a target detection result in a case that a matching degree between a first image and a target image meets a first preset condition.

The target detection result is a detection result corresponding to the target image.

It may be understood that the target image may be an image that has been stored in the electronic device and is corresponding to a target object obtained last time by the electronic device, or may be another image corresponding to the target object stored in the electronic device.

Optionally, in some embodiments of the present invention, that the matching degree between the first image and the target image meets the first preset condition may be: a matching degree between scenario information of the first image and scenario information of the target image is greater than a preset matching degree threshold; or may be: an image similarity between the first object and the target object is greater than a preset similarity threshold. The first image includes the first object, and the target image includes the target object.

It may be understood that the scenario information includes at least one of image background information and image shooting location information. The image background may be considered as an image area except the object in an image, namely, an image in the first image except the first object and an image in the target image except the target object. The image background information is parameter information such as brightness, chrominance or sharpness of the part of the image; and the image shooting location information is information about a geographic location in which an electronic device is located when the image was shot.

In some embodiments, in a case that the matching degree between the scenario information of the first image and the scenario information of the target image is greater than the preset matching degree threshold, it may be that a matching degree between brightness of the first image and brightness of the target image is greater than the preset matching degree threshold; it may also be that a matching degree between a chrominance of the first image and a chrominance of the target image is greater than the preset matching degree threshold; it may also be that a matching degree between a sharpness of the first image and a sharpness of the target image is greater than the preset matching degree threshold; and it may also be that a matching degree between an image shooting location of the first image and an image shooting location of the target image is greater than the preset matching degree threshold.

In some other embodiments, the first object may be a facial area of a user in the first image, and the target object may be a facial area of the user in the target image. In a case that the image similarity between the first object and the target object is greater than the preset similarity degree threshold, it may be determined that the matching degree between the first image and the target image meets the first preset condition.

In this embodiment of the present invention, after the first image information is obtained, the electronic device may determine the matching degree between the first image and the target image. In addition, in a case that the matching degree between the first image and the target image meets the first preset condition, it may be considered that the matching degree between the first image and the target image is relatively high, and in this case, there is no need to detect the skin information in the first image again. Instead, the target detection result corresponding to the target image is directly output, thereby improving the output efficiency of the detection result of the electronic device.

S103: Output a first detection result in a case that the matching degree between the first image and the target image does not meet the first preset condition, where the first detection result is a detection result corresponding to the first image.

Optionally, in some embodiments of the present invention, that the matching degree between the first image and the target image does not meet the first preset condition may include any one of the following:

a matching degree between scenario information of the first image and scenario information of the target image is less than or equal to a preset matching degree threshold, or an image similarity between the first object and the target object is less than or equal to a preset similarity threshold.

In this embodiment of the present invention, if the matching degree between the first image and the target image does not meet the first preset condition, it may be considered that the matching degree between the first image and the target image is lower. Therefore, to ensure the accuracy of the skin detection result, the skin information in the first image may be detected, and the first detection result corresponding to the first image is finally output.

In the embodiments of the present invention, the electronic device obtains the first image information (including the skin information) of the first object, and determines the matching degree between the first image and the target image. In the case that the matching degree between the first image and the target image does not meet the first preset condition, the first detection result corresponding to the first image is output; or in the case that the matching degree between the first image and the target image meets the first preset condition, the skin detection may not be performed on the first object, and the detection result corresponding to the target object is directly output, thereby improving the output speed of the detection result of the electronic device and improving user experience.

In some embodiments of the present invention, to make a final output target detection result more accurate, the output target detection result may also be a detection result obtained by performing information fusion processing on a first detection result and a second detection result. The first detection result is a detection result corresponding to the skin information in the first image, and the second detection result is a detection result corresponding to the skin information in the target image.

In this embodiment of the present invention, since the output target detection result is the detection result after the information fusion processing is performed on the first detection result and the detection result corresponding to the skin information in the target image, it may, to a certain extent, avoid the situation that the skin detection performed by a same user in a same scenario will obtain greatly different skin detection results, so that the target detection result output by the electronic device is more accurate, thereby improving the user experience.

To timely obtain the target image and the detection result corresponding to the target image, in some embodiments of the present invention, before S101, the detection result output method further includes the following steps:

store the target image and the detection result corresponding to the target image.

It may be understood that the target image stored herein may include a parameter value of the target object in the target image. For example, in a case that the target object is a human, parameters such as facial features size and distance of the target object may be stored, and the background information of the target image and the shooting location information of the target image may also be stored, so as to improve a comparison speed when compared with the first image information.

In some other embodiments of the present invention, before S101, the electronic device may also detect a facial image of the first object. Specific details are referred to the detection result output method shown in FIG. 2.

Figure 2:
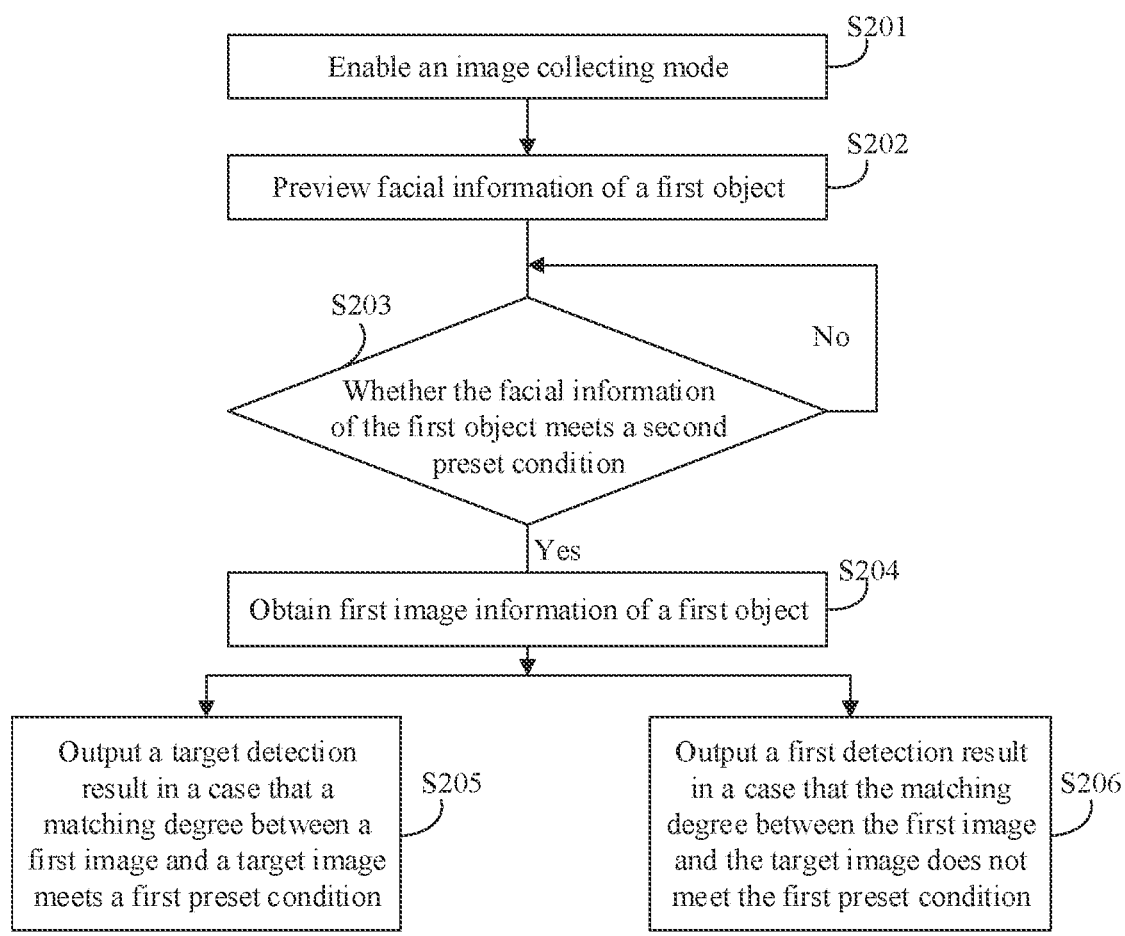
FIG. 2 is a schematic flowchart of a detection result output method according to another embodiment of the present invention.

As shown in FIG. 2, FIG. 2 is a schematic flowchart of a detection result output method according to another embodiment of the present invention. The method includes: S201 to S206.

S201: Enable an image collecting mode.

Optionally, in some embodiments of the present invention, before obtaining a first image, an electronic device also needs to enable the image collecting mode, for example, enabling a camera.

S202: Preview a facial image of a first object.

S203: Detect whether the facial image of the first object meets a second preset condition, where the second preset condition includes at least one of the following: an integrity of the facial image is greater than a preset integrity threshold, an illumination value of the facial image is greater than a preset illumination threshold, and a sharpness of the facial image is greater than a preset sharpness threshold. If yes, S204 is performed; and if not, continue to perform S203.

S204: Obtain first image information of the first object in a case that the second preset condition is met.

The first image information includes skin information of the first object, and the first image information further includes a first image.

S205: Output a target detection result in a case that a matching degree between a first image and a target image meets a first preset condition.

The target detection result is a detection result corresponding to the target image.

S206: Output a first detection result in a case that the matching degree between the first image and the target image does not meet the first preset condition.

The first detection result is a detection result corresponding to the first image.

S204 to S206 and S101 to S103 are the same steps, which are not described herein again.

In this embodiment of the present invention, by detecting the facial image of the first object before obtaining the first image, the electronic device may obtain an image more suitable for skin detection, thereby improving the accuracy of a skin detection report.

Figure 3:
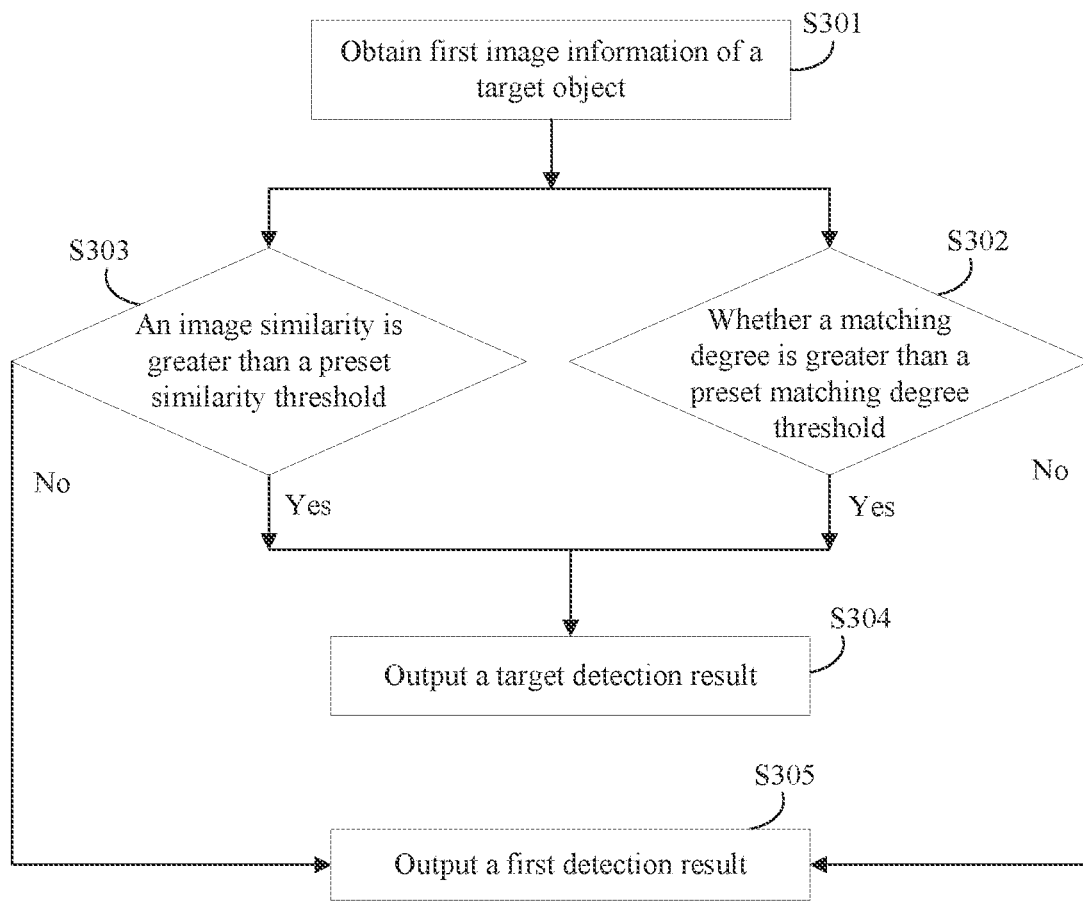
FIG. 3 is a schematic flowchart of a detection result output method according to still another embodiment of the present invention.

The following describes a detection result output method according to still another embodiment of the present invention in detail with reference to a schematic flowchart of a detection result output method as shown in FIG. 3.

As shown in FIG. 3, FIG. 3 is a schematic flowchart of a detection result output method according to still another embodiment of the present invention. The detection result output method includes: S301 to S305.

S301: Obtain first image information of a first object.

It should be understood that, before S301, an electronic device may also perform the steps as described in the above S201 to S203, and then perform S301 in a case that a facial image of the first object meets a second preset condition.

S302: Determine whether a matching degree between scenario information of a first image and scenario information of a target image is greater than a preset matching degree threshold. If yes, S304 is performed; and if not, S305 is performed.

It should be understood that, a higher preset matching degree threshold indicates a better matching between the scenario information of the first image and the scenario information of the target image. The preset matching degree threshold may be set according to needs of an actual application scenario, and there is no limitation herein.

S303: Determine whether an image similarity between the first object and the target object is greater than a preset similarity threshold. If yes, S304 is performed; and if not, S305 is performed.

Optionally, in some embodiments of the present invention, an image histogram may be used to calculate the image similarity between the first image and the target image. The image histogram is used to represent brightness distribution, plotting a quantity of pixels for each brightness value in the image.

For example, the image similarity between the first image and the target image may be calculated by using an image gradient histogram, an image brightness histogram, and an image color histogram.

S304: Output a target detection result. The target detection result is a detection result corresponding to the target image.

S305: Output a first detection result. The first detection result is a result corresponding to skin information in the first image.

In the embodiments of the present invention, the electronic device obtains the first image information (including the skin information) of the first object, and determines the matching degree between the first image and the target image from two perspectives of the scenario information or the image similarity. In the case that the matching degree between the first image and the target image does not meet the first preset condition, the first detection result corresponding to the first image is output; or in the case that the matching degree between the first image and the target image meets the first preset condition, the skin detection may not be performed on the first object, and the detection result corresponding to the target object is directly output, thereby improving the output speed of the detection result of the electronic device and improving user experience.

Figure 4:
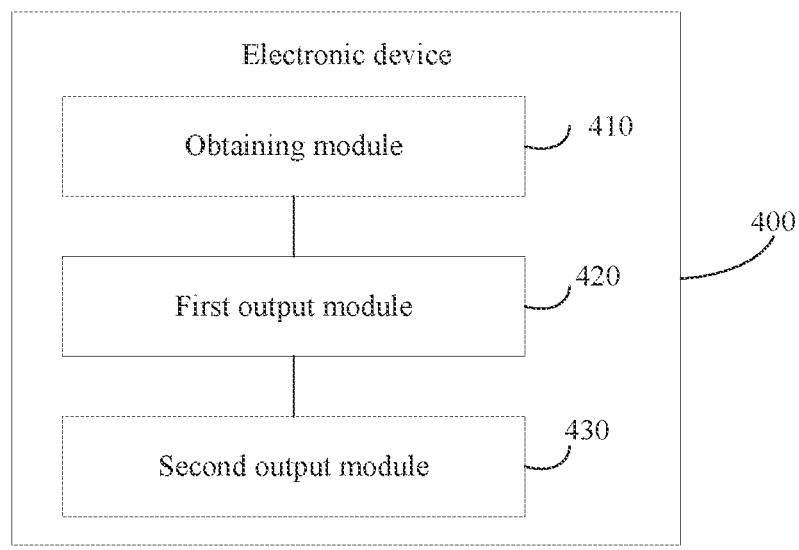
FIG. 4 is a schematic structural diagram of an electronic device according to an embodiment of the present invention.

Based on the specific implementation of the detection result output method according to the foregoing embodiments, the present invention further provides a specific implementation of an electronic device correspondingly. Referring to FIG. 4.

FIG. 4 is a schematic structural diagram of an electronic device according to an embodiment of the present invention. As shown in FIG. 4, the electronic device 400 includes:

- an obtaining module 410, configured to obtain first image information of a first object, where the first image information includes skin information of the first object;
- a first outputting module 420, configured to output a target detection result in a case that a matching degree between a first image and a target image meets a first preset condition; and
- a second outputting module 430, configured to output a first detection result in a case that the matching degree between the first image and the target image does not meet the first preset condition, where the target detection result is a detection result corresponding to the target image, and the first detection result is a detection result corresponding to the first image.

In the embodiments of the present invention, the electronic device obtains the first image information (including the skin information) of the first object, and determines the matching degree between the first image and the target image. In the case that the matching degree between the first image and the target image does not meet the first preset condition, the first detection result corresponding to the first image is output; or in the case that the matching degree between the first image and the target image meets the first preset condition, the skin detection may not be performed on the skin information of the first object, and the detection result corresponding to the target object is directly output, thereby improving the output speed of the detection result of the electronic device and improving user experience.

Optionally, in some embodiments of the present invention, that the matching degree between the first image and the target image meets the first preset condition includes:

- a matching degree between scenario information of the first image and scenario information of the target image is greater than a preset matching degree threshold;
- alternatively, an image similarity between the first object and the target object is greater than a preset similarity threshold, where the first image includes the first object, and the target image includes the target object.

Optionally, in some embodiments of the present invention, the scenario information includes at least one of the followings:

- image background information and image shooting location information.

Optionally, in some embodiments of the present invention, the electronic device 400 further includes:

- a detecting module, configured to detect whether a facial image of the first object meets a second preset condition; and
- the obtaining module 410 is specifically configured to:
- in a case that the facial image meets the second preset condition, obtain the first image information of the first object, where the second preset condition includes at least one of the following: an integrity of the facial image is greater than a preset integrity threshold, an illumination value of the facial image is greater than a preset illumination threshold, and a sharpness of the facial image is greater than a preset sharpness threshold.

Optionally, in some embodiments of the present invention, the electronic device 400 further includes:

- a storage module, configured to store the target image and a detection result corresponding to the target image.

Figure 5:
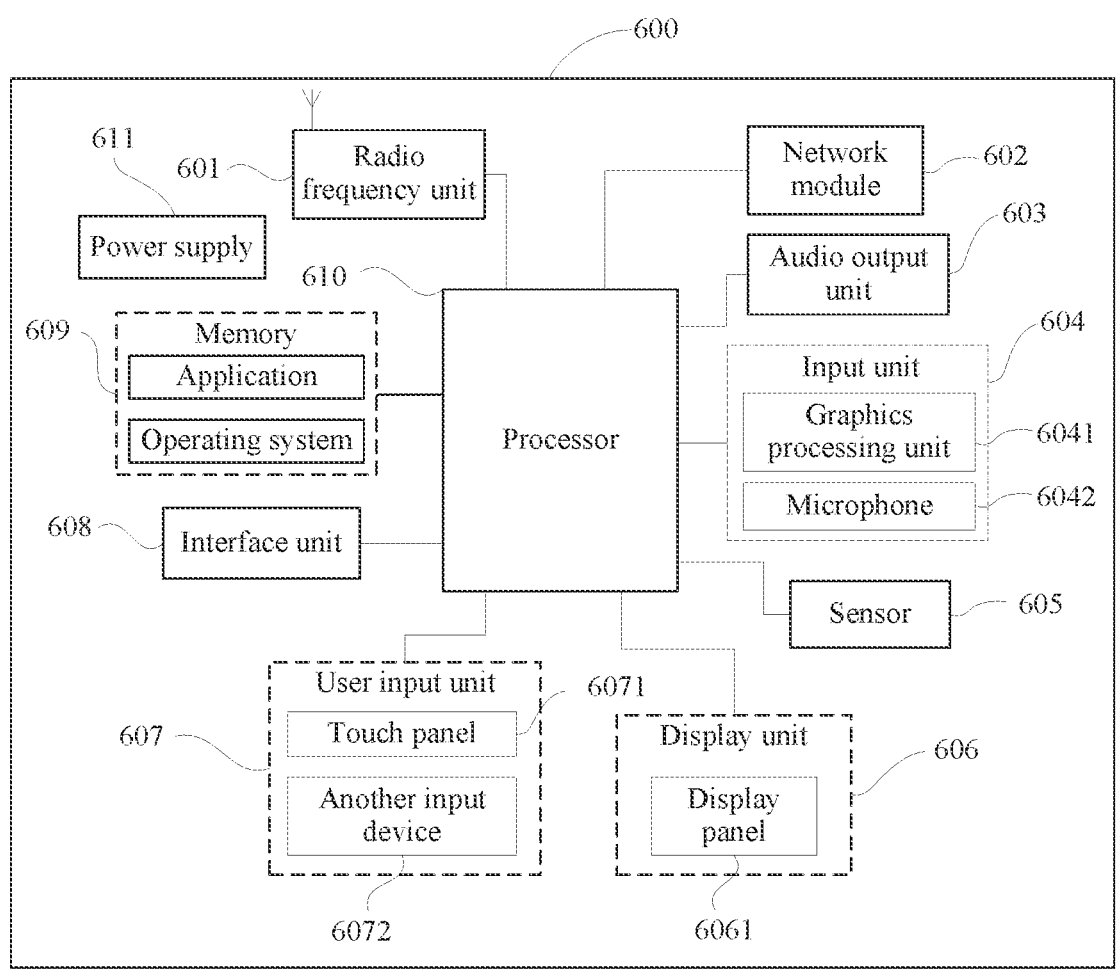
FIG. 5 is a schematic structural diagram of hardware of an electronic device according to embodiments of the present invention.

The following describes a hardware structure of an electronic device according to various embodiments of the present invention in detail with reference to FIG. 5.

As shown in FIG. 5, FIG. 5 is a schematic structural diagram of hardware of an electronic device according to various embodiments of the present invention.

The electronic device 600 includes but is not limited to components such as a radio frequency unit 601, a network module 602, an audio output unit 603, an input unit 604, a sensor 605, a display unit 606, a user input unit 607, an interface unit 608, a memory 609, a processor 610, and a power supply 611. A person skilled in the art may understand that a structure of the electronic device shown in FIG. 5 constitutes no limitation on the electronic device, and the electronic device may include more or fewer components than those shown in the figure, or have a combination of some components, or have a different component arrangement. In this embodiment of the present invention, the electronic device includes but is not limited to a mobile phone, a tablet computer, a notebook computer, a palmtop computer, an in-vehicle terminal, a wearable device, a pedometer, and the like.

The processor 610 is configured to obtain first image information of a first object, where the first image information includes skin information of the first object; output a target detection result in a case that a matching degree between a first image and a target image meets a first preset condition; and output a first detection result in a case that the matching degree between the first image and the target image does not meet the first preset condition. The target detection result is a detection result corresponding to the target image, and the first detection result is a detection result corresponding to the first image.

In the embodiments of the present invention, the electronic device obtains the first image information (including the skin information) of the first object, and determines the matching degree between the first image and the target image. In the case that the matching degree between the first image and the target image does not meet the first preset condition, the first detection result corresponding to the first image is output; or in the case that the matching degree between the first image and the target image meets the first preset condition, the skin detection may not be performed on the first object, and the detection result corresponding to the target object is directly output, thereby improving the output speed of the detection result of the electronic device and improving user experience.

It should be understood that, in this embodiment of the present invention, the radio frequency unit 601 may be configured to receive and send information or receive and send a signal in a call process. Specifically, after downlink data from a base station is received, the processor 610 processes the downlink data. In addition, uplink data is sent to the base station. Generally, the radio frequency unit 601 includes but is not limited to: an antenna, at least one amplifier, a transceiver, a coupler, a low noise amplifier, a duplexer, and the like. In addition, the radio frequency unit 601 may communicate with a network and another device through a wireless communication system.

The electronic device provides users with wireless broadband Internet access through the network module 602, for example, helps users receive and send e-mails, browse web pages, and access streaming media.

The audio output unit 603 may convert audio data received by the radio frequency unit 601 or the network module 602 or stored in the memory 609 into an audio signal and output the audio signal as a sound. In addition, the audio output unit 603 can further provide an audio output (for example, call signal received sound or message received sound) related to a specific function performed by the electronic device 600. The audio output unit 603 includes a loudspeaker, a buzzer, a telephone receiver, and the like.

The input unit 604 is configured to receive an audio signal or a video signal. The input unit 604 may include a graphics processing unit (GPU) 6041 and a microphone 6042. The graphics processing unit 6041 processes image data of a static image or video obtained by an image collecting apparatus (such as, a camera) in a video collecting mode or an image collecting mode. A processed image frame may be displayed on the display unit 606. The image frame processed by the graphics processing unit 6041 may be stored in the memory 609 (or another storage medium) or sent by using the radio frequency unit 601 or the network module 602. The microphone 6042 may receive sound and can process such sound into audio data. The processed audio data may be converted in a call mode into a format that can be sent by the radio frequency unit 601 to a mobile communication base station for outputting.

The electronic device 600 further includes at least one sensor 605 such as a light sensor, a motion sensor, and another sensor. Specifically, the light sensor includes an ambient light sensor and a proximity sensor. The ambient light sensor may adjust brightness of the display panel 6061 based on brightness of ambient light. The proximity sensor may turn off the display panel 6061 and/or backlight when the electronic device 600 moves close to an ear. As a motion sensor, an accelerometer sensor may detect magnitude of acceleration in various directions (usually three axes), may detect magnitude and the direction of gravity when stationary, may be configured to identify electronic device postures (such as switching between a landscape mode and a portrait mode, related games, and magnetometer posture calibration), may perform functions related to vibration identification (such as a pedometer and a knock), and the like. The sensor 605 may further include a fingerprint sensor, a pressure sensor, an iris sensor, a molecular sensor, a gyroscope, a barometer, a hygrometer, a thermometer, an infrared sensor, or the like. Details are not described herein again.

The display unit 606 is configured to display information input by a user or information provided for a user. The display unit 606 may include a display panel 6061. The display panel 6061 may be configured in a form of a liquid crystal display (LCD), an organic light-emitting diode (OLED), or the like.

The user input unit 607 may be configured to: receive entered digital or character information, and generate key signal input related to a user setting and function control of the electronic device. Specifically, the user input unit 607 includes a touch panel 6071 and another input device 6072. The touch panel 6071 is also referred to as a touchscreen, and may collect a touch operation performed by a user on or near the touch panel (for example, an operation performed by a user on the touch panel 6071 or near the touch panel 6071 by using any proper object or accessory, for example, a finger or a stylus). The touch panel 6071 may include two parts: a touch detection apparatus and a touch controller. The touch detection apparatus detects a touch location of the user, detects a signal brought by the touch operation, and sends the signal to the touch controller. The touch controller receives touch information from the touch detection apparatus, converts the touch information into touch point coordinates, sends the touch point coordinates to the processor 610, and receives and executes a command sent by the processor 610. In addition, the touch panel 6071 may be implemented in various types such as a resistor, a capacitor, an infrared ray, or a surface acoustic wave. The user input unit 607 may include other input devices 6072 in addition to the touch panel 6071. Specifically, the another input device 6072 may include but is not limited to: a physical keyboard, function keys (for example, a volume control key and an on/off key), a trackball, a mouse, or a joystick. Details are not described herein.

Further, the touch panel 6071 may cover the display panel 6061. When detecting the touch operation on or near the touch panel 6071, the touch panel transmits the touch operation to the processor 610 to determine a type of a touch event, and then the processor 610 provides corresponding visual output on the display panel 6061 based on the type of the touch event. Although in FIG. 5, the touch panel 6071 and the display panel 6061 are configured as two independent components to implement input and output functions of the electronic device, in some embodiments, the touch panel 6071 and the display panel 6061 can be integrated to implement the input and output functions of the electronic device. Details are not limited herein.

The interface unit 608 is an interface for connecting an external apparatus with the electronic device 600. For example, the external apparatus may include a wired or wireless headset jack, an external power supply (or a battery charger) port, a wired or wireless data port, a storage card port, a port for connecting an apparatus having an identification module, an audio input/output (I/O) port, a video I/O port, a headset jack, or the like. The interface unit 608 may be configured to receive an input (for example, data information and power) from an external apparatus and transmit the received input to one or more elements in the electronic device 600 or may be configured to transmit data between the electronic device 600 and the external apparatus.

The memory 609 may be configured to store a software program and various data. The memory 609 may mainly include a program storage area and a data storage area. The program storage area may store an operating system, an application required by at least one function (for example, a sound play function or an image display function), and the like. The data storage area may store data (for example, audio data or an address book) or the like created based on use of a mobile phone. In addition, the memory 609 may include a high-speed random access memory, and may further include a nonvolatile memory, for example, at least one magnetic disk storage device, a flash storage device, or another volatile solid-state storage device.

The processor 610 is a control center of the electronic device, connects all parts of the entire electronic device by using various interfaces and lines, and performs various functions of the electronic device and data processing by running or executing a software program and/or a module that are/is stored in the memory 609 and by invoking data stored in the memory 609, to monitor the electronic device entirely. The processor 610 may include one or more processing units. Preferably, an application processor and a modem processor may be integrated into the processor 610. The application processor mainly processes an operating system, a user interface, an application, and the like. The modem processor mainly processes wireless communications. It can be understood that, alternatively, the modem processor may not be integrated into the processor 610.

The electronic device 600 may further include the power supply 611 (for example, a battery) supplying power to each component. Preferably, the power supply 611 may be logically connected to the processor 610 by using a power management system, so as to implement functions such as charging management, discharging management, and power consumption management by using the power management system.

In addition, the electronic device 600 includes some function modules not shown. Details are not described herein.

Preferably, the embodiments of the present invention further provide an electronic device, including a processor 610, a memory 609, and a computer program that stored in the memory 609 and capable of running on the processor 610. When the computer program is executed by the processor 610, the foregoing processes of the detection result output method embodiment are implemented, and a same technical effect can be achieved. To avoid repetition, details are not described herein again.

An embodiment of the present invention further provides an electronic device, configured to implement the foregoing processes of the detection result output method embodiment, and a same technical effect can be achieved. To avoid repetition, details are not described herein again.

An embodiment of the present invention further provides a computer-readable storage medium. The computer-readable storage medium stores a computer program, where when the computer program is executed by a processor, the processes of the foregoing detection result output method embodiment are implemented, and a same technical effect can be achieved. To avoid repetition, details are not described herein again. For example, the computer-readable storage medium includes a non-transitory computer-readable storage medium, such as a read-only memory (ROM), a random access memory (RAM), a magnetic disk, an optical disc, or the like.

An embodiment of the present invention further provides a computer program product. The computer program product is executed by a processor to implement the foregoing detection result output method embodiment, and a same technical effect can be achieved. To avoid repetition, details are not described herein again.

The foregoing describes the aspects of the present invention with reference to flowcharts and/or block diagrams of the method, the apparatus (system), and the computer program product according to the embodiments of the present invention. It should be understood that each block in the flowchart and/or block diagram and a combination of blocks in the flowchart and/or block diagram may be implemented by a computer program instruction. These computer program instructions may be provided for a general-purpose computer, a dedicated computer, or a processor of another programmable data processing apparatus to generate a machine, so that when these instructions are executed by the computer or the processor of the another programmable data processing apparatus, specific functions/actions in one or more blocks in the flowcharts and/or in the block diagrams are implemented. The processor may be but is not limited to a general purpose processor, a dedicated processor, a special application processor, or a field programmable logic circuit. It should be further understood that each block in the block diagram or the flowchart and a combination of blocks in the block diagram or the flowchart may be implemented by using dedicated hardware that performs a specified function or operation, or may be implemented by using a combination of dedicated hardware and a computer instruction.

It should be noted that, in this specification, the terms "include", "comprise", or any of their variants are intended to cover a non-exclusive inclusion, such that a process, a method, an article, or an apparatus that includes a list of elements not only includes those elements but also includes other elements that are not expressly listed, or further includes elements inherent to such process, method, article, or apparatus. In the absence of more restrictions, an element defined by the statement "including a . . . " does not preclude the presence of other identical elements in the process, method, article, or apparatus that includes the element.

By means of the foregoing description of the embodiments, a person skilled in the art may clearly understand that the method in the foregoing embodiments may be implemented by software in addition to a necessary universal hardware platform. Certainly, the method in the foregoing embodiments may also be implemented by hardware. However, in many cases, the former is a preferred embodiment. Based on such an understanding, the technical solutions of the present invention essentially or the part contributing to existing technologies may be implemented in a form of a software product. The computer software product is stored in a storage medium (such as a ROM/RAM, a magnetic disk, or an optical disc) and includes several instructions for instructing a terminal (which may be a mobile phone, a computer, a server, an air conditioner, or a network device) to execute the methods described in the embodiments of the present invention.

The embodiments of the present invention are described above with reference to the accompanying drawings, but the present invention is not limited to the foregoing specific implementations. The foregoing specific implementations are merely exemplary instead of restrictive. Under enlightenment of the present invention, a person of ordinary skill in the art may make many forms without departing from the objective of the present invention and the protection scope of claims, all of which fall within the protection of the present invention.

The ivnention claimed is:

1. A detection result output method, comprising:
obtaining, by an electronic device, first image information of a first object using a camera component, wherein the first image information comprises skin information of the first object; wherein the first image information further comprises a first image;
wherein the skin information comprises at least one of: skin moisture, elasticity index, or oiliness index;
skipping detecting, by the electronic device, the skin information of the first object in the first image, and outputting, by the electronic device through a display unit, a stored target detection result as a detection result of the skin information of the first object in the first image in a case that a matching degree between the first image and a target image meets a first preset condition; wherein the target detection result is a detection result of skin information of a target object in the target image; wherein the target image is an image that has been stored in the electronic device and is corresponding to the target object obtained last time by the electronic device, or is another image corresponding to the target object stored in the electronic device; and
detecting, by the electronic device, the skin information of the first object in the first image, and outputting, by the electronic device through the display unit, a first detection result in a case that the matching degree between the first image and the target image does not meet the first preset condition, wherein the first detection result is a detection result corresponding to the first image;

wherein the method further comprises:

before the obtaining, by an electronic device, first image information of a first object, previewing a facial image of the first object; and detecting, by the electronic device, whether the facial image of the first object meets a second preset condition;

wherein the obtaining, by an electronic device, first image information of a first object comprises:

in a case that the facial image meets the second preset condition, obtaining, by the electronic device, the first image information of the first object, wherein the second preset condition comprises at least one of the following: an integrity of the facial image is greater than a preset integrity threshold, an illumination value of the facial image is greater than a preset illumination threshold, and a sharpness of the facial image is greater than a preset sharpness threshold.

2. The method according to claim 1, wherein that the matching degree between a first image and a target image meets a first preset condition comprises:

a matching degree between scenario information of the first image and scenario information of the target image is greater than a preset matching degree threshold;

alternatively, an image similarity between the first object and the target object is greater than a preset similarity threshold, wherein the first image comprises the first object, and the target image comprises the target object.

3. The method according to claim 2, wherein the scenario information comprises at least one of the following:

image background information and image shooting location information.

4. The method according to claim 3, wherein the image background information comprises at least one of the following:

brightness information, chrominance information, and sharpness information of other areas other than an object in an image.

5. The method according to claim 3, wherein the image shooting location information comprises:

information about a geographic location in which an electronic device is located when the image was shot.

6. The method according to claim 1, before the obtaining, by an electronic device, first image information of a first object, further comprising:

storing, by the electronic device, the target image and the target detection result.

7. The method according to claim 6, wherein the storing, by the electronic device, the target image comprises:

storing, by the electronic device, at least one of a parameter value of the target object, background information of the target image, and shooting location information of the target image.

8. An electronic device, comprising a processor, a memory, and a computer program that is stored in the memory and capable of being executed the processor, wherein the computer program is executed by the processor to implement:

obtaining first image information of a first object using a camera component, wherein the first image information comprises skin information of the first object;

wherein the first image information further comprises a first image; wherein the skin information comprises at least one of: skin moisture, elasticity index, or oiliness index;

skipping detecting the skin information of the first object in the first image, and outputting, through a display unit, a stored target detection result as a detection result of the skin information of the first object in the first image in a case that a matching degree between the first image and a target image meets a first preset condition; wherein the target detection result is a detection result of skin information of a target object in the target image; wherein the target image is an image that has been stored in the electronic device and is corresponding to the target object obtained last time by the electronic device, or is another image corresponding to the target object stored in the electronic device; and detecting the skin information of the first object in the first image, and outputting, through the display unit, a first detection result in a case that the matching degree between the first image and the target image does not meet the first preset condition, wherein the first detection result is a detection result corresponding to the first image;

wherein the computer program is further executed by the processor to implement:

previewing a facial image of the first object; and detecting whether the facial image of the first object meets a second preset condition; and in a case that the facial image meets the second preset condition, obtaining the first image information of the first object, wherein the second preset condition comprises at least one of the following: an integrity of the facial image is greater than a preset integrity threshold, an illumination value of the facial image is greater than a preset illumination threshold, and a sharpness of the facial image is greater than a preset sharpness threshold.

9. The electronic device according to claim 8, wherein that the matching degree between a first image and a target image meets a first preset condition comprises:

a matching degree between scenario information of the first image and scenario information of the target image is greater than a preset matching degree threshold;

alternatively, an image similarity between the first object and the target object is greater than a preset similarity threshold, wherein the first image comprises the first object, and the target image comprises the target object.

10. The electronic device according to claim 8, wherein the scenario information comprises at least one of the following:

image background information and image shooting location information.

11. The electronic device according to claim 10, wherein the image background information comprises at least one of the following:

brightness information, chrominance information, and sharpness information of other areas other than an object in an image.

12. The electronic device according to claim 10, wherein the image shooting location information comprises:

information about a geographic location in which an electronic device is located when the image was shot.

13. The electronic device according to claim 8, wherein the computer program is further executed by the processor to implement:
storing the target image and the target detection result.

14. The electronic device according to claim 13, wherein the computer program is further executed by the processor to implement:
storing at least one of a parameter value of the target object, background information of the target image, and shooting location information of the target image.

15. A non-transitory computer-readable storage medium, wherein the computer-readable storage medium stores a computer program, and the computer program is executed by a processor of an electronic device, to implement:
obtaining first image information of a first object using a camera component of the electronic device, wherein the first image information comprises skin information of the first object; wherein the first image information further comprises a first image; wherein the skin information comprises at least one of: skin moisture, elasticity index, or oiliness index;
skipping detecting the skin information of the first object in the first image, and outputting, through a display unit of the electronic device, a stored target detection result as a detection result of the skin information of the first object in the first image in a case that a matching degree between the first image and a target image meets a first preset condition; wherein the target detection result is a detection result of skin information of a target object in the target image; wherein the target image is an image that has been stored in the electronic device and is corresponding to the target object obtained last time by the electronic device, or is another image corresponding to the target object stored in the electronic device; and
detecting the skin information of the first object in the first image, and outputting, through the display unit of the electronic device, a first detection result in a case that the matching degree between the first image and the target image does not meet the first preset condition, wherein the first detection result is a detection result corresponding to the first image;
wherein the computer program is further executed by the processor of the electronic device, to implement:
previewing a facial image of the first object; and
detecting whether the facial image of the first object meets a second preset condition; and
in a case that the facial image meets the second preset condition, obtaining the first image information of the first object, wherein the second preset condition comprises at least one of the following: an integrity of the facial image is greater than a preset integrity threshold, an illumination value of the facial image is greater than a preset illumination threshold, and a sharpness of the facial image is greater than a preset sharpness threshold.

* * * * *